United States Patent [19]

Chretien et al.

[11] Patent Number: 6,001,799
[45] Date of Patent: Dec. 14, 1999

[54] METHOD OF TREATING HEPATITIS C IN NON-RESPONDERS TO INTERFERON TREATMENT

[75] Inventors: Paul B. Chretien, Rockville, Md.; Milton Mutchnick, West Bloomfield, Mich.

[73] Assignees: SciClone Pharmaceuticals, Inc., San Mateo, Calif.; The Board of Governors of Wayne State University, Detroit, Mich.

[21] Appl. No.: 08/027,500

[22] Filed: Mar. 5, 1993

Related U.S. Application Data

[63] Continuation-in-part of application No. 07/759,544, Sep. 13, 1991, abandoned.

[51] Int. Cl.⁶ .......................... A61K 38/03; A61K 38/16
[52] U.S. Cl. .................................. 514/2; 514/12
[58] Field of Search .......................................... 514/12, 2

[56] References Cited

U.S. PATENT DOCUMENTS 5,849,696  12/1998  Chretien et al. ........................ 514/12

FOREIGN PATENT DOCUMENTS 0331934  9/1989  European Pat. Off. .

OTHER PUBLICATIONS

European Search Report dated Dec. 15, 1992.
Eichberg et al., "Effect of Thymosin . . . Hepatitis B Carriers", *Chemical Abst.*, vol. 106, No. 15, Apr. 1987, Abst. No. 117943h pp. 487–488.
Kuo, G., et al., *Science*, 244:362–4 (1989).
Alter, H.H., in Zuckerman, A.J., ed., *Viral Hepatitis and Liver Disease*, Allen K. Liss, New York, 1988, pp. 537–42.
Kortez. R.L., et al., *Gastroenterology*, 88:1251–4 (1985).
Pappas, S.C., *J. Med. Virol.*, 15:1–9 (1985).
Stokes, P., et al. *Gastroenterology*, 92:1783 Abstract (1987).
Hoofnagle, J.H., et al. *New England Journal of Medicine*, 315:1575–8 (1986).
Thomson, J., *Lancet*, 1:539–41 (1987).
Kiyosawa, K., et al., in Zukerman, A., ed., *Viral Hepatitis and Liver Disease*, Allen K. Liss, NY., 1983 pp. 895–7.
Hoffnagle, J.H., et al., *Sem. Liver Dis.*, 9:259–263 (1985).
Low, T.L.K., et al., Thymosing: Structure, Function and Therapeutic Application:, *Thymus*, 6:27–42 (1984).
Goldstein, et al., *Proc. Nat'l Acad. Sci. (USA)*, 69:1800–1803 (1972).
Wetzel, R. et al., *Biochemistry*, 19:6096–6104 (1980).
Low, T.L.K., et al., *J. Biol. Chem.*, 254:981–6 (1979).
Schulof, R.S., et al., in *The Lymphocyte*, Allen J. Liss Inc., NY 1981, pp. 191–215.
Koutab, N.M., et al., *Immunopharm.*, 16:97–105 (1988).
Favilli, C. et al., *Cancer Immunol. Immunother.*, 20:189–92 (1985).
Marshall, G.D., et al., *J Immunol.*, 126:741–4 (1981).
Baxevanis, C.N., et al., *Immunopharm.*, 13:133–41 (1987).
Svedsky, L.P., *Eur. J. Immunol.*, 12:244–7 (1982).
Goldstein, A.L., et al., *Transp. Proc.*, 9:1141 (1977).
Cohen, N.H., et al., *J. Amer. Med. Assoc.*, 241:1813–5 (1979).
Schulof, R.S., et al., *J. Biol. Response Modifiers*, 4:147–58 (1985).
Gravenstein, S., et al., *JAGS*, 37:1–8 (1989).
Korba, B.E., et al., *Hepatology*, 12: Abs. 880 (1990).
Weiner, A.J., et al., *Lancet*, 335:1–3 (1990).
Knodell, R.G., et al., *Hepatology*, 1:431–5 (1981).
Ulrich, P., et al., *J. Clin. Invest.*, 86:1609–14 (1990).
Mutchnick, M.G., et al. *Clin. Immunol. Immunopathol.*, 23:626–33 (1982).
Serrate, S.A., et al., *J. Immunol.*, 1939:233–43 (1987).
Sztein, M.B., et al., *Proc. Nat'l Acad. Sci (USA)*, 83:6107–6111 (1986).
Davis etal., *The New England Journal of Medicine*, 321:1501–1506 (1989).
C. Albert, *Gastroenterology Journal Club*, pp. 2–8, Apr. 1991.
Blendis, MD, *Gastroenterology Journal Club*, p. 12.
S.H. Caldwell, MD, *Gastroenterology Journal Club*, pp. 9–12, Apr. 1991.
Di Bisceglie, MD, *The New England Journal of Medicine*, 321:1506–1510 (1989).
P. Farci, et al., *The New England Journal of Medicine*, 325:98–104 (1991).
P. Marcellin, et al., *Hepatology*, 13:393–398 (1991).
M.J. Alter, *The New England Journal of Medicine*, 321:1538–1540 (1989).

*Primary Examiner*—David Guzo
*Attorney, Agent, or Firm*—Rothwell, Figg, Ernst & Kurz, p.c.

[57] ABSTRACT

A method of treating Hepatitis C by administering an immune system-potentiating dose of at least one Thymosin or system-potentiating Thymosin fragment to a mammal infected with Hepatitis C virus, which Hepatitis C infection in the mammal is non-responsive to treatment with interferon alone.

5 Claims, No Drawings

METHOD OF TREATING HEPATITIS C IN NON-RESPONDERS TO INTERFERON TREATMENT

This application is a continuation-in-part of Ser. No. 07/759,544, filed Sep. 13, 1991, now abandoned.

BACKGROUND OF THE INVENTION

1. Field of the Invention

This invention relates generally to the pharmacological treatment of hepatitis C virus infection in patients.

2. Description of the Related Art

Hepatitis C virus (HCV), the putative agent in the majority of post-transfusion acquired hepatitis, has been recently defined by a new serologic assay. Kuo, G., et al., *Science*, 244:362–4 (1989). Despite improvement in the quality of the blood-donor pool and the recent implementation of testing of donated blood, the current estimated incidence of acute infection among persons receiving transfusions is 5 to 10%. Alter, H. J., in Zuckerman, A. J., ed., *Viral Hepatitis and Liver Disease*, Allen K. Liss, New York, 1988, pp. 537–42. Chronic hepatitis develops in at least half the patients with acute HCV infection (representing about 90% of patients with non-A, non-B hepatitis (NANB)), and cirrhosis develops in at least 20% of this group. Thus, of the approximately 3 million persons who receive transfusions in the United States each year, acute hepatitis C will develop in about 150,000. Chronic hepatitis C will develop in at least 75,000 of these, and among them cirrhosis will develop in more than 15,000. Among patients with post-transfusion hepatitis, up to about 90% are positive for the HCV antibody. Davis, G. L., et al., *New England Journal of Medicine*, 321:1501–6 (1989). Patients with sporadic NANB hepatitis (no specific risk factors) are also very likely to have the anti-HCV antibody. Kuo, et al. (1989) above. While most of the patients who contract hepatitis C will have subclinical or mild disease, approximately 50% will progress to a chronic disease state characterized by fluctuating serum transaminase abnormalities and inflammatory lesions on liver biopsy. By some estimates, cirrhosis will develop in up to about 20% of this group. Koretz, R. L., et al., *Gastroenterology*, 88:1251–4 (1985).

With the aim of halting or slowing the progression of HCV-related diseases, a variety of drugs have been evaluated in recent years. Both acyclovir and corticosteroids (which are beneficial in autoimmune chronic active hepatitis) are ineffective. Pappas, S. C., *J. Med. Virol.*, 15:1–9 (1985); Stokes, P., et al., *Gastroenterology*, 92:1783 abstract (1987).

To date, α-interferon (IFA) appears to be the most promising candidate, although not necessarily the final answer. Hoofnagle, J. H., et al., in *Viral Hepatitis: 1981 International Symposium*, Philadelphia, Franklin Institute Press, 1982, pp. 573–83; Hoofnagle, J. H., et al., *New England Journal of Medicine*, 315:1575–8 (1986); Thomson, J., *Lancet*, 1:539–41 (1987); Kiyosawa, K., et al., in Zuckerman, A., ed., *Viral Hepatitis and Liver Disease*, Allen K. Liss, New York, 1983, pp. 895–7. Hoofnagle, J. H., et al., *Sem. Liver Dis.*, 9:259–263 (1985). The interferons are host proteins made in response to viral infections as well as other antigenic stimuli. They are classified by their cell of origin as well as their antigenicity. α-Interferon is made by lymphoblastoid cells, β-interferon by fibroblasts, and γ-interferon by T-cells. Subtypes in each group are based on antigenic/structural characteristics. Recombinant forms for each group have been developed and are commercially available. A pilot study utilizing IFA on ten patients with well-characterized post-transfusion NANB hepatitis was reported in 1986 by Hoofnagle et al. (Hoofnagle, J. H., et al., *New England Journal of Medicine*, 315:1575–8 (1986)). In this study, eight of ten patients improved their serum alanine transaminase (ALT) levels within one month of starting therapy. IFA therapy consisted of 5 million units (MU) daily in seven of the patients and one MU daily in three patients. In all subjects the dose was gradually reduced to 1 MU daily and then finally switched to an alternate day or every three day regimen. In three patients who had post-treatment liver biopsies, the specimen showed a marked improvement in the degree of portal inflammation and loss of parenchymal hepatocytic necrosis. Side effects were common at the 5 MU/day dose and virtually absent at 1 MU/day.

The effects of recombinant human interferon α in a prospective, randomized, double-blind, placebo-controlled trial in patients with well-documented chronic HCV infection has recently been carried out. Di Bisceglie, A. M., et al., *New England Journal of Medicine*, 321:1506–10 (1989). Forty-one patients were enrolled in the trial, 37 of whom were later found to have antibody to HCV. Twenty-one patients received interferon α (2 MU) subcutaneously three times weekly for six months, and twenty received placebo. The mean serum ALT and the histological features of the liver improved significantly in the patients treated with interferon, but not in the patients given placebo. Ten patients treated with interferon (48%) had a complete response, defined as a decline in mean serum ALT to the normal range during therapy; three others had a decrease in mean ALT of more than 50%. After treatment ended, however, serum ALT usually returned to pretreatment levels; six to twelve months after the discontinuation of interferon therapy, only two patients (10%) still had normal values. The authors concluded that interferon α therapy is beneficial in reducing disease activity in chronic hepatitis C; however, the beneficial responses are often transient and side effects are known to appear.

In another, broader study, chronic hepatitis C (NANB hepatitis) in 166 patients was treated with either 3 MU or 1 MU of recombinant human α-IFA three times weekly for 24 weeks or to no treatment. The serum ALT level became completely normal in 22 of the 26 patients (85%) who responded to treatment with 3 MU of interferon, and nine of the sixteen patients (56%) responded to treatment with 1 MU. The patients who received 3 MU of interferon had histologic improvement because of the regression of lobular and periportal inflammation. However, relapse within six months after the completion of treatment occurred in 51% of the patients treated with 3 MU of interferon and in 44% of those treated with 1 MU. Davis, G. L., et al., *New England Journal of Medicine*, 321:1501–06 (1989). These authors concluded that a 24-week course of interferon therapy is effective in controlling disease activity in many patients with hepatitis C, although relapse after the cessation of treatment is common.

A multi-center randomized control trial of recombinant human α-IFN in patients with chronic NANB hepatitis has been reported recently. Marcellin, P., et al., *Hepatology*, 13:393–97 (1991). Patients were randomly assigned to no treatment or to 1 to 3 MU of α-interferon given three times a week for 24 weeks. Forty-five patients (75%) were positive for antibody to HCV. During the 24 week treatment period, mean serum ALT levels decreased in both treatment groups, but the decrease was statistically significant only in the 3 MU group. However, at 24 weeks, the proportion of patients with normal ALT levels was similar in the 3 MU group (39%) and the 1 MU group (45%) and both were significantly higher than in controls (0%). Repeat liver biopsy specimens showed a significant decrease in the severity of histological changes in the higher dose group but not in the lower dose group or in controls. However, after treatment, the mean ALT levels rose in both treated groups. The proportion of patients with normal ALT levels at week 48 was 28% in the 3 MU group and 20% in the 1 MU group. The authors conclude that a dose of 3 MU was superior to 1 MU of α-interferon given three times per week for 24 weeks in inducing improvements in serum ALT levels and liver histological examinations. However, relapse in disease activity occurred in approximately half of the responders when interferon was stopped. The response to α-interferon did not correlate with the source of infection or with the presence or absence of anti-HCV antibody titres in patient sera.

It is clear, therefore, that while a-interferon has a beneficial effect on the course of HCV infection, this effect is frequently only transient. Therefore, new modalities are necessary in order permanently to eradicate the effects of hepatitis C virus on the patient.

Another class of polypeptide immune modifiers derived from the thymus gland, the thymosins, has been shown to trigger maturational events in lymphocytes, to augment T-cell function and to promote reconstitution of immune defects. Low, T. L. K., et al., "Thymosins: Structure, Function and Therapeutic Application", *Thymus*, 6:27–42 (1984).

Thymosin Fraction Five (TF-5), originally described by Goldstein et al. (*Proc. Nat'l Acad. Sci. (USA)*, 69:1800–1803 (1972)), is a partially purified extract of bovine thymus containing at least 40 peptide components, 20 of which have been purified to homogeneity or near homogeneity; it contains about 0.6% of Thymosin α-1 ($THN\alpha_1$). Low, 1984, above.

$THN\alpha_1$, initially isolated from TF-5, has been sequenced and chemically synthesized. Wetzel, R., et al., *Biochemistry*, 19:6096–6104 (1980). Its sequence is highly homologous in mice, calves and humans. $THN\alpha_1$ is a 28 amino acidic polypeptide with a molecular weight of 3100 that has shown activity qualitatively similar to TF-5 in modulating the immune system. Low, T. L. K., et al., *J. Biol. Chem.*, 254:981–6 (1979). $THN\alpha_1$ has potent immunologic activity, including stimulation of α- and γ-interferon production, increasing macrophage migration inhibitory factor production, inducing expression of T-cell markers, including IL-2 receptors, and improving T-cell helper cell activity. Schulof, R. S., et al., in The *Lymphocyte*, Allen J. Liss Inc., New York, 1981, pp. 191–215; Low, T. L. K., et al., in "Thymosins: Structure, Function and Therapeutic Applications", *Thymus*, 6:27–43 (1984); Koutab, N. M., et al., *Immunopharm.*, 16:97–105 (1988). Studies in mice have demonstrated a synergistic effect of $THN\alpha_1$ and interferon on natural killer-cell activity in immunosuppressed mice. Favilli, C., et al., *Cancer Immunol. Immunother.*, 20:189–92 (1985). TF-5 and $THN\alpha_1$ can influence immunoregulatory T-cell function, promote production of interferon-α, interferon-γ and interleukin-2 by human lymphocytes and increase interleukin-2 receptor expression. Marshall, G. D., et al., *J. Immunol.*, 126:741–4 (1981); Mutchnick, M. G., et al., *Clin. Immunol. Immunopathol.*, 23:626–33 (1982); Sztein, M. B., et al., *Proc. Nat'l Acad. Sci. (USA)*, 83:6107–6111 (1986); Serrate, S. A., et al., *J. Immunol.*, 1939:2338–43 (1987); Baxevanis, C. N., et al., *Immunopharm.*, 13:133–41 (1987); and, Svedersky, L. P., *Eur. J. Immunol.*, 12:244–7 (1982).

Clinical trials of TF-5 and $THN\alpha_1$ as primary or adjunctive therapy in patients with immunodeficiency or cancer indicate that these agents enhance immune responsiveness and augment specific lymphocyte functions. Clinical trials of TF-5 and purified $THN\alpha_1$ have been underway for a number of years. Early trials in patients with cancer or immunodeficiency states were encouraging, though not definitive. Goldstein, A. L., et al., *Transp. Proc.*, 9:1141 (1977); Barrett, D. J., et al., *J. Pediatr.*, 97:61 (1980); and Cohen, M. H., et al., *J. Amer. Med. Assoc.*, 241:1813–5 (1979). $THN\alpha_1$ use has been described in a randomized trial of patients with nonsmall cell lung cancer. Patients were treated with $THN\alpha_1$ at a dose of 900 μgrams/m$^2$ subcutaneously twice weekly or daily for two weeks and then twice weekly after completing a course of radiotherapy. The only side effect of $THN\alpha_1$ was mild burning at the injection site in three patients. This was attributed to the drug lot and may have been due to the carrier preparation. Relapse-free survival and overall survival were greater in both $THN\alpha_1$ treatment groups than in the placebo group; some restoration of radiation-suppressed immune function was also noticed. There was no increase in T-cell numbers associated with this. Schulof, R. S., et al. *J. Biol. Response Modifiers*, 4:147–58 (1985).

Recent double-blind, randomized trials with thymosins have been performed in elderly men in an effort to increase response to influenza vaccine. Gravenstein, S., et al., *JAGS*, 37:1–8 (1989). Patients received synthetic $THN\alpha_1$ subcutaneously twice weekly starting at the time the influenza vaccine was given. At six weeks post-vaccine, those patients randomized to receive the drug had higher levels of antibody to influenza than controls. This difference was accentuated in the very elderly (ages 77–99). No clinical or biochemical toxicity was observed in drug recipients.

There are preliminary reports that thymosins may be effective against infections caused by hepatitis viruses other than HCV. In an animal model of viral hepatitis, the woodchuck infected with the Woodchuck Hepatitis Virus, $THN\alpha_1$ suppressed viral DNA replication, but produced no improvement in clinical parameters. Korba, B. E., et al., *Hepatology*, 12:Abs. 880 (1990). In a pilot clinical trial with patients with Chronic Active Hepatitis B caused by the hepatitis B virus (HBV), patients treated for a year with $THN\alpha_1$ (5 patients) or with TF-5 (2 patients) showed a marked decrease in serum ALT; 6 of the 7 patients also showed reduced levels of serum HBV DNA, and 5 of 6 patients initially positive for serum hepatitis B surface antigen (HBSAg) subsequently cleared this antigen. Mutchnick, M. C., et al., *Hematology*, 10:Abs. 575 (1989). No suggestion was made in these abstracts that the thymosins would be effective against any other hepatitis viruses.

There remains, therefore, an important need in the art for a new modality for the treatment of HCV infections in mammals; this modality is disclosed below.

SUMMARY OF THE INVENTION

A treatment modality for HCV infections has been devised for mammals infected with Hepatitis C virus, which Hepatitis C infection in said mammals is non-responsive to treatment with interferon. The treatment modality comprises the administration to mammals of immune system-potentiating doses of one or more thymosins, alone or in combination with interferon therapy.

It is thus an object of this specification to disclose compositions and methods for the treatment of acute or chronic HCV infections in mammals with one or more members of the thymosin family of biological response modifiers.

It is another object of this specification to disclose compositions and methods for the treatment of acute or chronic HCV infections in mammals comprising combination therapy with one or more thymosins and one or more interferons.

These and other objects will become apparent by reference to the specification and to the appended claims.

DESCRIPTION OF THE INVENTION

A novel modality for treating HCV infection in mammals has been devised, comprising the administration to such mammals of one or more thymosins at doses which potentiate immune responses, alone or in combination with antiviral doses of one or more interferons.

By the term "thymosins" is meant any or all of the immune system potentiating polypeptides naturally occurring in the thymus gland or produced by chemical or recombinant means, or fragments derived from any of these polypeptides. By the term "mammals" is meant any mammalian subject, including human and animal patients, requiring treatment for hepatitis C infection. "Mammal" and "subject" are used interchangeably.

Thymosin preparations suitable for treating HCV infections include TF-5, THN$\alpha_1$ and fragments thereof, e.g., C-terminal 4-28 and 15-28, and N-terminal 1-8, 1-14 and 1-20 fragments. These may be obtained from Alpha-1 Biomedicals Inc., Foster City, Calif.

Subjects, e.g., human patients, may receive the thymosin by subcutaneous injection or infusion, at appropriate intervals for an appropriate period of time. The thymosin is administered to mammals infected with hepatitis C virus in amounts which facilitate or promote in vivo inactivation of hepatitis C virus. A pharmaceutical dosage unit of an immune system-potentiating amount of a thymosin, such as TF-5, can be from about 900 to about 1200 mg/m$^2$ body surface area in a pharmaceutically acceptable carrier. A pharmaceutical dosage unit of an immune system-potentiating amount of a thymosin, such as THN$\alpha_1$ or immune system-potentiating fragments thereof, can be from about 900 to about 1200 µg/m$^2$ body surface area in a pharmaceutically-acceptable carrier. Lyophilized preparations of thymosins or fragments which contain mannitol and phosphate buffer are dissolved in diluent prior to dispensing. Thymosins in diluent should remain stable for at least six months when stored in a refrigerator. It is convenient to dispense thymosin solutions in one ml dose vials. Some patients may require about eight vials per month.

For a typical human patient, an administration regimen of twice weekly (e.g., Monday and Thursday) subcutaneous injection of about 1500 to about 1700 µg of THN$\alpha_1$ or fragments therefrom is convenient. Dosages and length of treatment can be flexible, and can be determined by the subject's clinical response to the thymosins.

The course of the disease and its response to drug treatments may be followed by clinical examination and laboratory findings. As elevated serum alanine aminotransferase (ALT) and aspartate aminotransferase (AST) are known to occur in uncontrolled hepatitis C, and as a complete response to treatment is generally defined as the normalization of these serum enzymes, particularly ALT (Davis, G. L., et al., *New England Journal of Medicine*, 321:1501–6 (1989)), progress of treatment with thymosins is conveniently followed by this art-recognized test performed, e.g., on a sequential multiple analyzer.

Another means of evaluating subjects having antibodies to HCV (not all subjects with hepatitis C have detectable antibody to HCV—Weiner, A. J., et al., *Lancet*, 335:1–3 (1990)) is to periodically test subjects, sera for the titer of these antibodies. Anti-HCV antibodies may be tested by the currently available C 100-3 test (Kuo, G., et al., *Science*, 244:362–4 (1989)), by an Elisa test (Ortho Diagnostic Systems, Raritan, N.J.) or by a recombinant assay (RIBA-1 and RIBA-2, Chiron Corporation, Emeryville, Calif.). Any suitable test may be used.

In order to follow the course of HCV replication in subjects in response to drug treatment, HCV RNA may be measured in serum samples by, for example, a nested polymerase chain reaction assay that uses two sets of primers derived from the NS3 and NS4 non-structural gene regions of the HCV genome. Farci, P., et al., *New England Journal of Medicine*, 325:98–104 (1991); Ulrich, P. P., et al., *J. Clin. Invest.*, 86:1609–14 (1990).

Other appropriate laboratory tests to follow the course of treatment are listed in Example 1 below.

Thymosin therapy may also be used in combination with interferon therapy, thereby combining the immune system potentiating effect of thymosins with the anti-viral effects of the interferons. An improved response rate at the currently used interferon doses would be beneficial, particularly in the light of dose-limiting side effects at higher doses of these proteins. An offshoot of this concept is the ability to achieve comparable efficacy with interferon plus thymosin at lower doses than would be required with interferon alone.

In this combination therapy regimen, one or more interferons (for example, recombinant interferon α-2b, Intron-A, Schering-Plough, Kenilworth, N.J.) is (are) administered subcutaneously to subjects, e.g., human patients, at doses ranging between about 1 MU and 3 MU along with or sequentially with one or more thymosins, preferably including THN$\alpha_1$, at a dose of about 900 to about 1200 µg/m$^2$ body surface area.

Although the example above speaks in terms of recombinant interferon α-2b, other anti-HCV-effective interferons such as α-, β- and γ-interferons, recombinant or naturally occurring, may be advantageously used in this invention.

This combination dose regimen is flexible, and depends on the clinical condition of the subject. Where subjects are refractory to the preferred dosage levels, these may be increased within the limits dictated by undesirable side effects. Typically, injections are made five times per week and continue until an acceptable response by the subject is realized.

Tests to determine the effectiveness of the combination therapy may be the same as those described above for thymosin treatment alone. In addition, histological examination of liver biopsy samples may be used as a second major criteria for evaluation. Knodell, R. G., et al., *Hepatology*, 1:431–5 (1981), whose Histological Activity Index (portal inflammation, piecemeal or bridging necrosis, lobular injury and fibrosis) provides a scoring method for disease activity.

The following examples are provided merely to illustrate the invention, and are not to be construed in any way as limiting the scope of invention as set forth in the specification and claims.

EXAMPLE 1

Preparation of Injectable Formulation

Pharmaceutical dosage units of 1 ml each are prepared from the ingredients shown in Table 1 below.

TABLE 1

| Active Ingredient | Amount Per mL |
|---|---|
| Thymosin α-1 | 0.0016 g |
| Inactive Ingredients | |
| mannitol, U.S.P. | 0.050 g |
| sodium phosphate dibasic, heptahydrate, U.S.P. | 0.002 g |
| sodium phosphate monobasic, monohydrate, U.S.P. | 0.0005 g |
| sodium phosphate dibasic, 2 mg/ml solution | |
| sodium phosphate monobasic, 0.5 mg/ml solution | |
| water for injection, U.S.P. | |

EXAMPLE 2

Treatment of Hepatitis C Infections in Human Patients with Thymosins and Interferons Adult patients with chronic active hepatitis C (CAHC) are randomized to one of four study groups, made up of about 40 patients per group. Selection criteria include: (1) patients are adults (at least 18 years of age); (2) serum ALT is elevated for at least six months prior to treatment with at least one value greater than twice the upper limit of normal in the laboratory doing the testing; (3) patients test positive for HCV antibody on two occasions and on a confirmatory test; and (4) liver biopsy within three months of treatment exhibits pathology consistent with chronic active hepatitis.

Exclusion criteria include: (1) recent use of other antiviral or immunosuppressive medication; (2) hemophilia, pregnancy or HIV infection, or other serious illness that could prevent completion of the course of treatment; (3) other forms of liver disease, including hepatitis A or B, α-1 antitrypsin deficiency, Wilson's disease, and hemochromatosis must be absent; (4) autoimmune markers (ANA, ASMA, AMA, anti-LKMI) must be absent or, if present, titers should be <1:40; (5) leukocyte deficiency (<3,000); (6) low absolute neutrophil count (<1,000); (7) low platelets (<75,000); (8) low Hb (<11 g/dL); (9) high bilirubin (>4 mg/dL); and (10) low serum albumin (3 g/dL).

The first of the four randomized groups receives interferon, preferably interferon α-2b, at a dose of 3 million units (MU) subcutaneously (SQ) on Mondays, Wednesdays and Fridays, and receives placebos on Tuesdays and Saturdays. The second group receives the same dose/schedule of interferon, plus a thymosin, preferably $THN\alpha_1$, at a dose of 900 $\mu g/m^2$ SQ on Tuesdays and Saturdays. The third group receives the same dose/schedule of a thymosin alone. The fourth group receives placebo treatment initially, but can be randomized to the three treatment groups thereafter. Interferons and thymosins can be recombinant.

Patients begin treatment while hospitalized for about one week, during which period side-effects are monitored.

Outpatient follow-up is initially at one week intervals for two weeks, then at two week intervals for two months, and then monthly for the remainder of the treatment period. At each visit the following lab tests are performed: CBC, platelet count, differential and ESR, ALT, AST, GGT, alkaline phosphatase, bilirubin, total bilirubin/albumin and HCV antibody. At monthly intervals serum γ-globulin, TSH, ANA and ASMA are assessed.

Drug toxicity is monitored on an ongoing basis using both clinical and laboratory parameters.

Within one month of completing the initial six months of treatment, patients undergo liver biopsy for pathological examination according to Knodell et al. above. This system provides a numerical scoring system of histological activity in patients with a symptomatic CAH.

At this time, control patients are randomized into three groups to receive one of the three treatment modalities, assuming that they still have CAH on follow-up liver biopsy, and that one arm of the study does not show highly significant positive or negative results on analysis at six months.

Patients in the treatment groups are followed to evaluate recrudescence of disease as evidenced by rising ALT levels. Patients who showed response in the initial six month treatment period, but who have a recurrence of the disease thereafter, are provided with additional therapy.

Additional serum or tissue tests are performed if possible: evaluation of antibodies to interferons and thymosins, polymerase chain reaction amplification of hepatitis C genome segments in liver biopsy samples, and quantitative evaluation of anti-hepatitis C serum titers.

EXAMPLE 3

The treatment protocol is as in Example 2, except that the interferon is used at the level of 2 MU, and the thymosin at 1050 $\mu g/m^2$.

EXAMPLE 4

The treatment protocol is as in Example 3, except that 1 MU of the interferon and 1200 $\mu g/m^2$ of the thymosin are used.

EXAMPLE 5

Analysis of Data

There are two primary criteria for response to therapy—normalization of ALT levels by the end of the treatment period (a partial response may be defined as a decrease of at least 50% of initial ALT), and histological improvement as determined by the Histological Activity Index (HAI) of Knodell et al. above.

This analysis provides a raw score ranging from 1 to 22 per sample. Paired data can be analyzed using the Wilcoxon paired-sample test. Additionally, samples can be classified into mild, moderate or reverse CAH, and improvement assessed using the Chi-square statistical analysis.

Life-table analysis is used to evaluate remission and relapse status in terms of normalization of ALT levels. Other continuous variables are analyzed using Student's t test. Dichotomous data are subjected to CHi square or Fisher's exact test, as is appropriate.

A power analysis was done to determine the number of patients in each test group in order to show predicted differences. Power analysis applied to an ANOVA using a power of 0.80 with α=0.05, coupled with prior studies of mean ALT levels and their variances, estimated a need for 21 to 52 patients in each test group to show a mean ALT difference of 15 IU/L. As 3 to 5% of patients are expected to drop out, and factoring in treatment of the control group after six months, 40 patients per group was arrived at.

EXAMPLE 6

Efficacy of Thymosin α-1 for treatment of Hepatitis C was shown in two Hepatitis C patients who were previous non-responders to α-interferon. These two patients were treated with Thymosin α-1 by subcutaneous injection of 1 mg thereof twice weekly, during administration three times weekly of 2 million units of α-IFN. After 6 months of treatment with Thymosin α-1, both patients showed a 50% reduction of serum alanine transaminase (ALT), thereby demonstrating efficacy of Thymosin α-1. Six other Hepatitis C patients treated as above showed a "complete response" to treatment after 6 months, with serum ALT levels reduced to normal. In three additional Hepatitis C patients treated as above, serum ALT levels were reduced 50% after 6 months. Six additional Hepatitis C patients treated as above did not respond sufficiently to achieve the threshold 50% reduction of serum ALT after 6 months.

What is claimed is:

1. A method of treating Hepatitis C comprising administering an immune system-potentiating dose of at least one Thymosin or immune system-potentiating Thymosin fragment to a mammal infected with Hepatitis C virus, which Hepatitis C infection in said mammal is non-responsive to treatment with interferon alone.

2. A method of claim 1, wherein the thymosin is selected from the group consisting of Thymosin Fraction Five, Thymosin α-1 and fragments thereof.

3. The method of claim 1, wherein said mammal is human, said Thymosin is Thymosin α-1, and said dose is about 1500 to about 1700 µg of said Thymosin α-1.

4. A method of claim 2, wherein said mammal is a human and said Thymosin Fraction Five is administered at a dose of about 900 to about 1200 mg/m$^2$ body surface area.

5. A method of claim 2, wherein said mammal is a human and said Thymosin α-1 or a fragment thereof is administered at a dose of about 900 to about 1200 µg/m$^2$ body surface area.

* * * * *